(12) United States Patent
Jou

(10) Patent No.: US 11,504,545 B2
(45) Date of Patent: Nov. 22, 2022

(54) METHOD FOR INHIBITING MELATONIN SECRETION AND ILLUMINATION DEVICE SUITABLE FOR BEING APPLIED IN LIGHT THERAPY FOR TREATING SEASONAL AFFECTIVE DISORDER

(71) Applicant: National Tsing Hua University, Hsinchu (TW)

(72) Inventor: Jwo-Huei Jou, Hsinchu (TW)

(73) Assignee: NATIONAL TSING HUA UNIVERSITY, Hsinchu (TW)

(*) Notice: Subject to any disclaimer, the term of this patent is extended or adjusted under 35 U.S.C. 154(b) by 517 days.

(21) Appl. No.: 16/585,276

(22) Filed: Sep. 27, 2019

(65) Prior Publication Data

US 2021/0008387 A1  Jan. 14, 2021

(30) Foreign Application Priority Data

Jul. 12, 2019 (TW) .................. 108124793

(51) Int. Cl.
*A61N 5/06* (2006.01)
*A61M 21/00* (2006.01)

(52) U.S. Cl.
CPC .......... *A61N 5/0618* (2013.01); *A61M 21/00* (2013.01); *A61M 2021/0044* (2013.01); *A61N 2005/0642* (2013.01); *A61N 2005/0662* (2013.01)

(58) Field of Classification Search
CPC ...... A61N 5/06; A61N 5/0613; A61N 5/0618; A61N 5/0622; A61N 2005/0626; A61N 2005/0627; A61N 2005/0629; A61N 2005/0642; A61N 2005/0643; A61N 2005/0648; A61N 2005/065; A61N 2005/0651; A61N 2005/0652; A61N 2005/0653; A61N 2005/0654; A61N 2005/0655; A61N 2005/0662; A61N 2005/0663; A61M 21/00; A61M 2021/0005; A61M 2021/0055
USPC ................ 607/88–91; 606/9–11; 128/898
See application file for complete search history.

(56) References Cited

U.S. PATENT DOCUMENTS

| | | | |
|---|---|---|---|
| 7,019,464 B2* | 3/2006 | Nevins | A61M 21/00 362/108 |
| 7,678,140 B2* | 3/2010 | Brainard | A61B 5/4848 607/91 |
| 8,465,531 B2* | 6/2013 | Aunio | A61N 5/0618 607/88 |
| 9,138,595 B2* | 9/2015 | Savage | A61N 5/0618 |

(Continued)

*Primary Examiner* — Ahmed M Farah

(57) ABSTRACT

Disclosures of the present invention describe a method for inhibiting melatonin secretion. In the present invention, an illumination device is particularly configured for emitting an illumination light with a specific wavelength that is in a range between 581 nm and 590 nm, and a variety of experimental data have proved that the illumination light functions as a melatonin secretion inhibitor. Therefore, the illumination device of the present invention is evidenced to be suitable for use in light therapy, so as to treat seasonal affective disorder (SAD) by way of inhibiting melatonin secretion. Briefly speaking, after a SAD patient receives the irradiation of the illumination light having wavelength ranged in 581-590 nm for a treatment course, the SAD patient is eventually leaded to stay in good spirits and a stable condition of emotion, thereby curing the abnormal symptoms of sleepiness and emotional disorder.

2 Claims, 18 Drawing Sheets

(56) References Cited

U.S. PATENT DOCUMENTS

| | | | |
|---|---|---|---|
| 10,315,043 B2* | 6/2019 | Pugh | A61B 5/14507 |
| 2010/0217358 A1* | 8/2010 | Hebert | A61M 21/00 |
| | | | 607/88 |
| 2012/0319593 A1* | 12/2012 | Jou | H05B 45/22 |
| | | | 315/294 |
| 2016/0158486 A1* | 6/2016 | Colbaugh | A61N 5/0618 |
| | | | 607/88 |
| 2016/0286616 A1* | 9/2016 | van de Ven | H05B 47/11 |
| 2017/0105265 A1* | 4/2017 | Sadwick | H05B 47/11 |
| 2021/0154490 A1* | 5/2021 | Paulsen | H05B 45/305 |

* cited by examiner

METHOD FOR INHIBITING MELATONIN SECRETION AND ILLUMINATION DEVICE SUITABLE FOR BEING APPLIED IN LIGHT THERAPY FOR TREATING SEASONAL AFFECTIVE DISORDER

BACKGROUND OF THE INVENTION

1. Field of the Invention

The present invention relates to the technology field of medical illuminations, and more particularly to a method for inhibiting melatonin secretion and an illumination device suitable for being applied in light therapy for treating seasonal affective disorder.

2. Description of the Prior Art

Winter depression, also known as seasonal affective disorder (SAD) or the "winter blues," is a subtype of depression or bipolar disorder that occurs at a certain time each year, usually in the fall or winter. Clinic reports have indicates that, there are some factors that causes or induces the occurrence of SAD, including lack of sunlight, insufficient secretion of serotonin and abnormal secretion of melatonin. Moreover, people suffering from SAD would tend to feel tired and have abnormal symptoms of sleepiness, weight gain and high appetite. So far there are some clinically-medical therapies for treating SAD, including light therapy (LT), drug therapy, cognitive behavioural therapy (CBT), and self-care therapy.

When a SAD patient receives the light therapy, the SAD patient is arranged to sit and face a light box, thereby facing the irradiation of an illumination light provided by the light box by a treatment frequency of 0.5 time/hour with a treatment course of 1-2 weeks. It is worth explaining that, light therapy is thought to affect brain chemicals linked to mood and sleep, thereby easing SAD symptoms. However, bright light radiated from the light box is commonly consists of several kinds of lights with high-energy and short wavelength, such as blue light and purple light. Accordingly, clinically-statistical data have reported that the light therapy would lead the SAD patient to suffer from some adverse symptoms like headache, dizziness, and eye fatigue. For above reasons, the SAD patient is recommended to receive the light therapy in the case of having a proper advisory of his attending doctor.

In addition, retinal light toxicity caused by exposure to light is a well-known entity and has been disclosed by certain research literatures. While the eye has adapted several mechanisms to protect itself from such damage, certain exposures to light can still result in temporal or permanent damage. FIG. 1 shows a curve graph of wavelength versus spectral-dependent photic retinopathy extent. From FIG. 1, it is able to observe that the short-wavelength light (<440 nm) cause the retina suffer from more photic retinopathy than that of the medium-wavelength light (530-545 nm) and/or long-wavelength light (560-580 nm). Therefore, the data provided in FIG. 1 have implied that, the probability of suffering from retinitis or other types of photic retinopathy for a man can be controlled to be a very low value as long as avoiding eyes from directly receiving short-wavelength light. Moreover, based on the data of FIG. 1, it is foreseeable that the SAD patient's retina specifically has a certain extent of damage that is caused in receiving the illumination of the light box. In other words, the SAD patient may further suffer from eye-related disease in spite of the fact that the seasonal affective disorder has been cured by the light therapy.

It is worth mentioning that, melatonin is one kind of hormone that is mainly synthesized by pineal gland. The beneficial properties of melatonin have captured the attention of clinicians during the past decades. Of special interest in this regard is its role in the cardiovascular system, especially in hypertension. On the other hand, it is also found that melatonin functions to regulate the sleep cycle, and further investigation also revealed that melatonin also plays an important role in heart rate regulating and muscle movement reducing. However, researches have found that exposure to short-wavelength light with high-energy (such as blue light) suppresses the production of the sleep hormone melatonin more than any other type of light.

Therefore, above descriptions have revealed that, it is helpful for curing winter depression by using a specific light source to provide an illumination to inhibit melatonin secretion in SAD patient's brain in the case of protecting retina from be damaged or stimulated by the illumination light. In view of that, inventors of the present application have made great efforts to make inventive research and eventually provided a method for inhibiting melatonin secretion and an illumination device suitable for being applied in light therapy for treating seasonal affective disorder.

SUMMARY OF THE INVENTION

The primary objective of the present invention is to disclose a method for inhibiting melatonin secretion. In the present invention, an illumination device is particularly configured for emitting an illumination light with a specific wavelength that is in a range between 581 nm and 590 nm, and a variety of experimental data have proved that the illumination light functions as a melatonin secretion inhibitor. Therefore, the illumination device of the present invention is evidenced to be suitable for use in light therapy, so as to treat seasonal affective disorder (SAD) by way of inhibiting melatonin secretion. Briefly speaking, after a SAD patient receives the irradiation of the illumination light having wavelength ranged in 581-590 nm for a treatment course, the SAD patient is eventually leaded to stay in good spirits and a stable condition of emotion, thereby curing the abnormal symptoms of sleepiness and emotional disorder.

In order to achieve the primary objective of the present invention, the inventor of the present invention provides an embodiment for the method for inhibiting melatonin secretion, comprising following steps:

providing a light source comprising a first lighting unit, wherein the first lighting unit is configured for emitting a first light with a first wavelength in a range between 581 nm and 590 nm;

controlling the light source to emit an illumination comprising the first light; and letting the illumination light function as an melatonin secretion inhibitor by guiding the illumination light to irradiate a seasonal affective disorder (SAD) patient.

In the embodiment of the method, the light source further comprises:

a second lighting unit for emitting a second light with a second wavelength in a range between 450 nm and 580 nm; and a third lighting unit for emitting a third light with a third wavelength in a range between 591 nm and 600 nm;

wherein the illumination light provided by the light source consists of the first light, the second light and the third light, and having a maximum color temperature of 1500K.

In the embodiment of the method, the first lighting unit is further configured to emit a second light with a second wavelength in a range between 450 nm and 580 nm and a third light with a third wavelength in a range between 591 nm and 600 nm, such that the illumination light provided by the light source consists of the first light, the second light and the third light, and having a maximum color temperature of 1500K.

Moreover, for achieving the primary objective of the present invention, the inventor of the present invention provides one embodiment for the method for illumination device, which is configured for use in light therapy for treating seasonal affective disorder, and comprises:
a light source, comprising a first lighting unit;
a driver unit, being electrically connected to the first lighting unit, so as to control the first lighting unit to emit a first light with a first wavelength in a range between 581 nm and 590 nm; and
a switch unit, being electrically connected to the driver unit for switching the driver unit to an enable state or a disable state.

In the embodiment of the illumination device, the light source further comprises:
a second lighting unit for emitting a second light with a second wavelength in a range between 450 nm and 580 nm; and
a third lighting unit for emitting a third light with a third wavelength in a range between 591 nm and 600 nm;
wherein the illumination light provided by the light source consists of the first light, the second light and the third light, and having a maximum color temperature of 1500K.

In the embodiment of the illumination device, the first lighting unit is further configured to emit a second light with a second wavelength in a range between 450 nm and 580 nm and a third light with a third wavelength in a range between 591 nm and 600 nm, such that the illumination light provided by the light source consists of the first light, the second light and the third light, and having a maximum color temperature of 1500K.

Furthermore, for achieving the primary objective of the present invention, the inventor of the present invention provides another one embodiment for the method for illumination device, which is configured for use in light therapy for treating seasonal affective disorder, and comprises:
a light source, comprising a first lighting unit, a second lighting unit and a third lighting unit;
a driver unit, being electrically connected to the first lighting unit, the second lighting unit and the third lighting unit, so as to control the first lighting unit, the second lighting unit and the third lighting unit to respectively emit a first light with a first wavelength in a range between 581 nm and 590 nm, a second light with a second wavelength in a range between 450 nm and 580 nm and a third light with a third wavelength in a range between 591 nm and 600 nm;
a switch unit, being electrically connected to the driver unit for switching the driver unit to an enable state or a disable state; and
a mode switching unit, being electrically connected to the driver unit, and being configured for switching the light source to operate in a normal illumination mode or a SAD treatment mode;
wherein when the light source is operated in the SAD treatment mode, the illumination light functions as an melatonin secretion inhibitor by guiding the illumination light to irradiate a seasonal affective disorder (SAD) patient;
wherein the illumination light provided by the light source consists of the first light, the second light and the third light in the case of the light source being operated in the normal illumination mode, and the illumination light having a maximum color temperature of 1500K.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a method for inhibiting melatonin secretion and an illumination device suitable for being applied in light therapy for treating seasonal affective disorder disclosed by the present invention, embodiments of the present invention will be described in detail with reference to the attached drawings hereinafter.

First Embodiment

Figure 2:
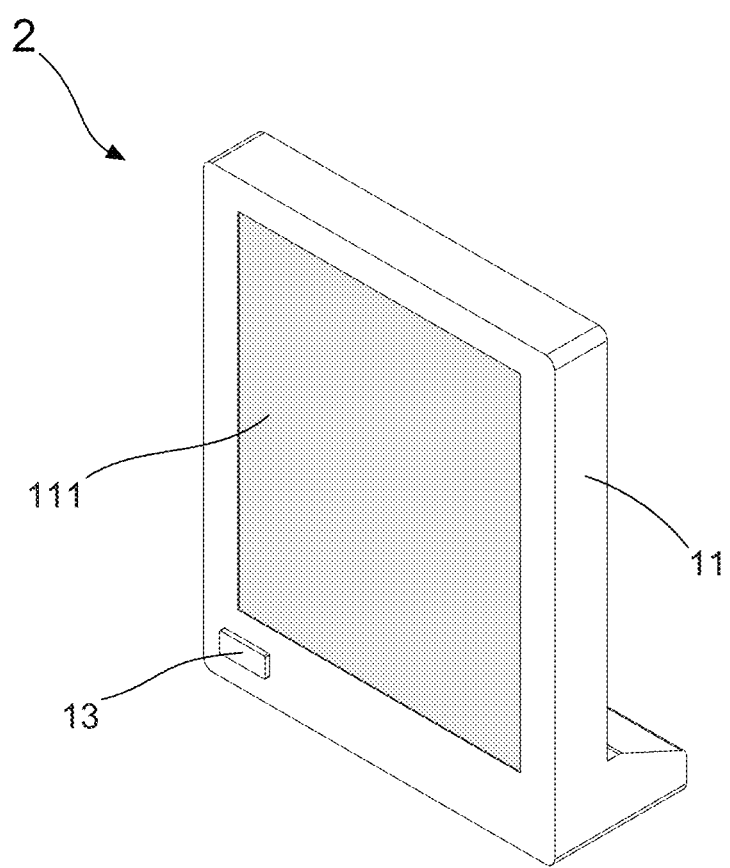
FIG. 2 shows a stereo diagram of a first embodiment of an illumination device suitable for being applied in light therapy for treating seasonal affective disorder according to the present invention.
Figure 3:
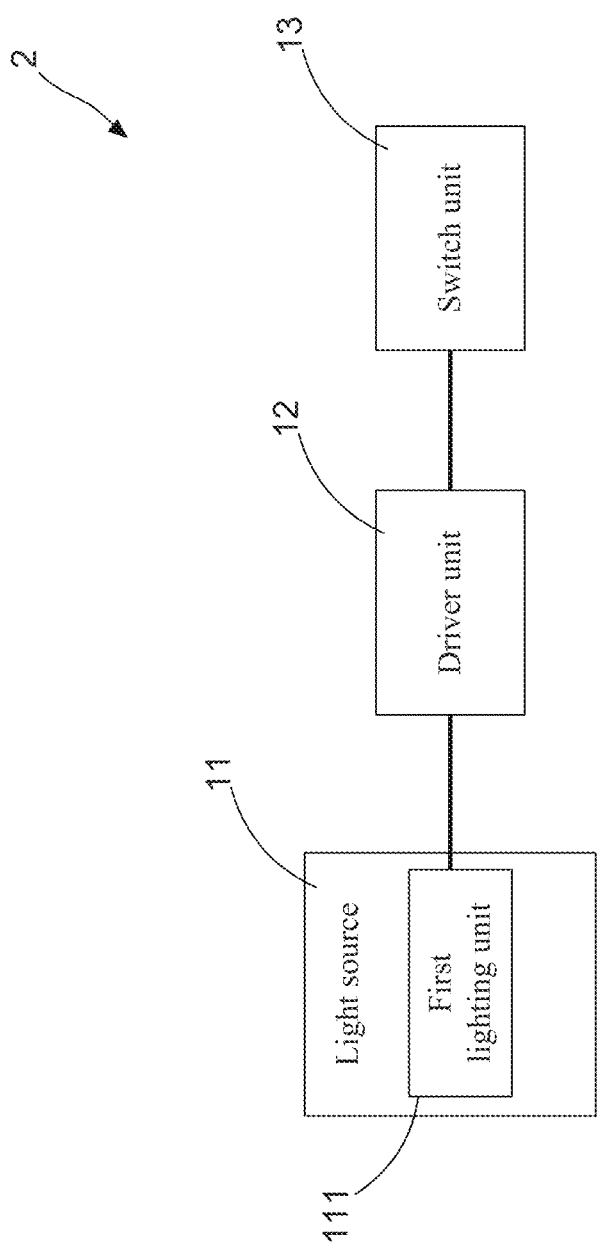
FIG. 3 shows a block diagram of the first embodiment of the illumination device according to the present invention.

With reference to FIG. 2, which shows a stereo diagram of a first embodiment of an illumination device suitable for being applied in light therapy for treating seasonal affective disorder according to the present invention. Moreover, FIG. 3 shows a block diagram of the first embodiment of the illumination device according to the present invention. Particularly, the present invention discloses a method for inhibiting melatonin secretion. When executing the method, it needs to firstly providing an illumination device 2 as shown in FIG. 2 and FIG. 3. From FIG. 2 and FIG. 3, it is able to know that the illumination device 2 is designed to be a light box for use in light therapy. The illumination device 2 mainly comprises a light source 11, a driver unit 12 and a switch unit 13, wherein the light source 11 comprises a first lighting unit 111, and the driver unit 12 is simultaneously coupled to the light source 11 and the switch unit 13. Therefore, the switch unit 13 is adopted for switching the driver unit 12 to an enable state or a disable state, and the driver unit 12 is configured to control the first lighting unit 111 to emit a first light with a first wavelength in a range between 581 nm and 590 nm. It is worth explaining that, the illumination device 2 comprising the light source 11 is evidenced, by a variety of experimental data, to be suitable for use in light therapy so as to treat seasonal affective disorder (SAD) by way of inhibiting melatonin secretion. In addition, engineers skilled in development and manufacture of illumination devices should know that, the light source 11 is driven by the driver unit 12 so as to provides an illumination light in the case of the illumination device 2 is normally operated, wherein the illumination light is a monochromatic light because of merely comprising the first light with the first wavelength in a range between 581 nm and 590 nm.

Figure 4:
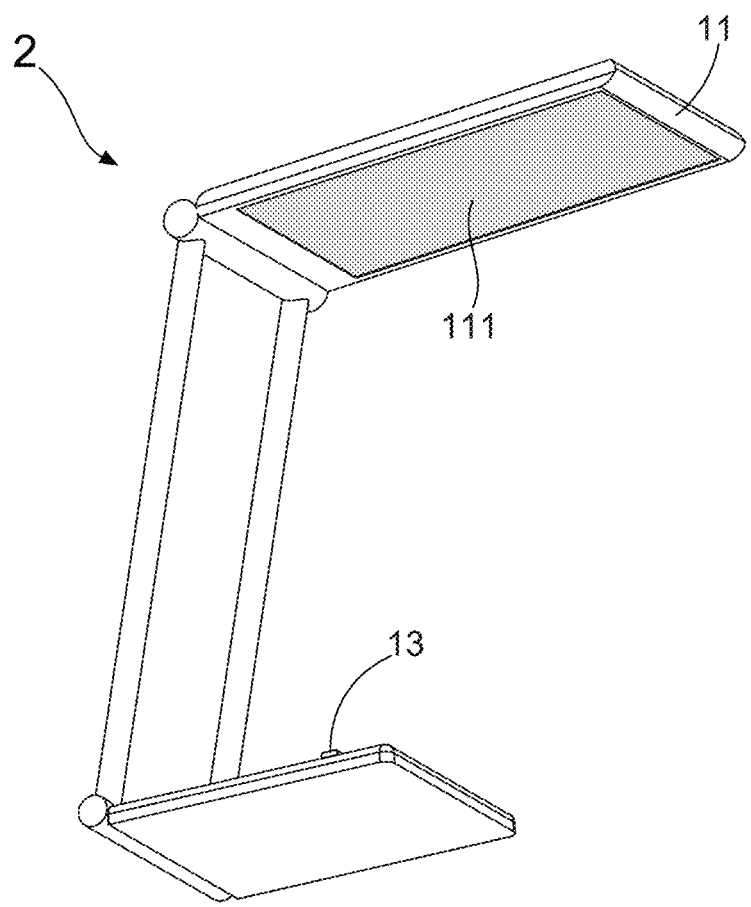
FIG. 4 shows a stereo diagram of a table lamp.
Figure 5:
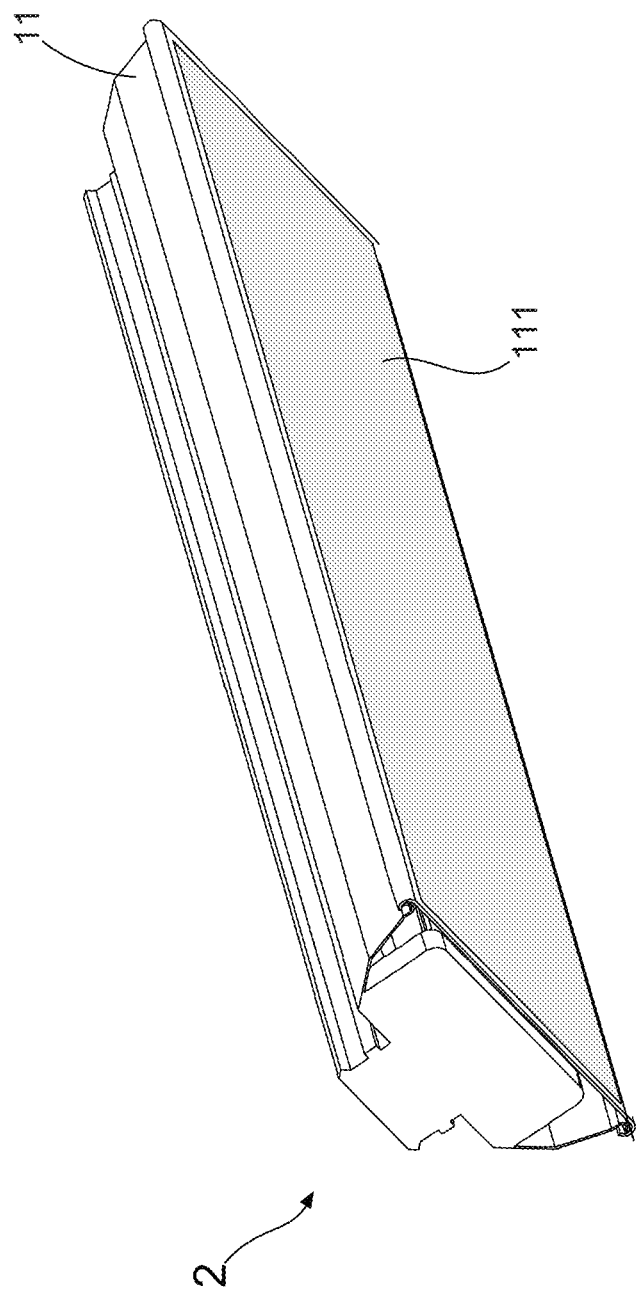
FIG. 5 shows a stereo diagram of a daylight lamp.

FIG. 4 and FIG. 5 show stereo diagrams of a table lamp and a daylight lamp, respectively. In spite of the fact that FIG. 3 depicts that the illumination device 2 of the present invention is particularly designed to a light box, it is not meant that the light box is the only one practicable embodiment of the illumination device 2 of the present invention. In a practicable embodiment, the illumination device 2 can also be designed to be a table lamp or a daylight lamp. It is understandable that, the illumination device 2 with a form of daylight lamp is adopted for providing an indoor illumination light in a room. On the other hand, the illumination device 2 with a form of table lamp is for use in providing an auxiliary illumination light to a user who is in reading or writing. Therefore, under the irradiation of the illumination light provided by the light source 11 of the illumination device 2, the melatonin (MLT) secretion in the brain of the user would be obviously inhibited, thereby gradually leading the user to stay in good spirits and a stable condition of emotion, such that the user tends to be clear-headed.

Accordingly, for assisting a user in keeping a clear mind, it is suggested to use the illumination device 2 to provide the illumination light to the person within 30-60 minutes after the user gets up. Alternatively, it is able to control the illumination device 2 to provide an indoor illumination light in a room where the user stays there in morning period. Therefore, under the irradiation of the illumination light provided by the light source 11 of the illumination device 2, the melatonin (MLT) secretion in the brain of the user would be obviously inhibited, thereby gradually leading the user to stay in good spirits and a stable condition of emotion, such that the user tends to be clear-headed. Moreover, it is foreseeable that, after a seasonal affective disorder (SAD) patient receives the irradiation of the illumination light having wavelength ranged in 581-590 nm for a treatment course, the abnormal symptoms of sleepiness and emotional disorder will be cured since the SAD patient is eventually leaded to stay in good spirits and a stable condition of emotion.

Second Embodiment

Figure 7:
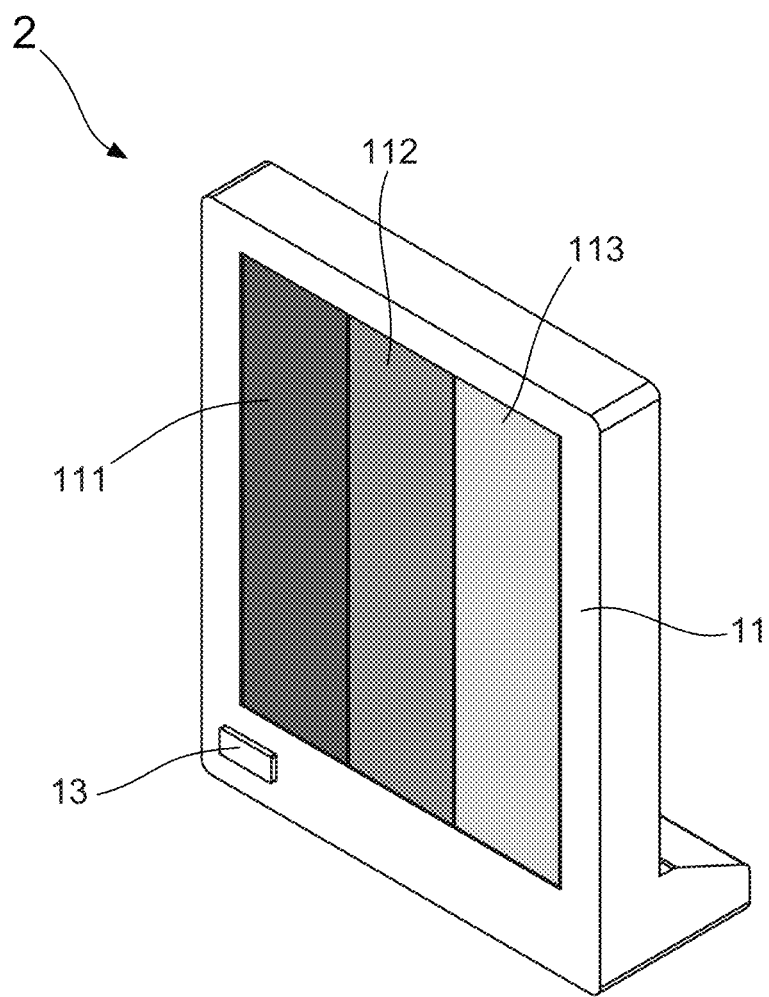
FIG. 7 shows a stereo diagram of a second embodiment of an illumination device suitable for being applied in light therapy for treating seasonal affective disorder according to the present invention.
Figure 8:
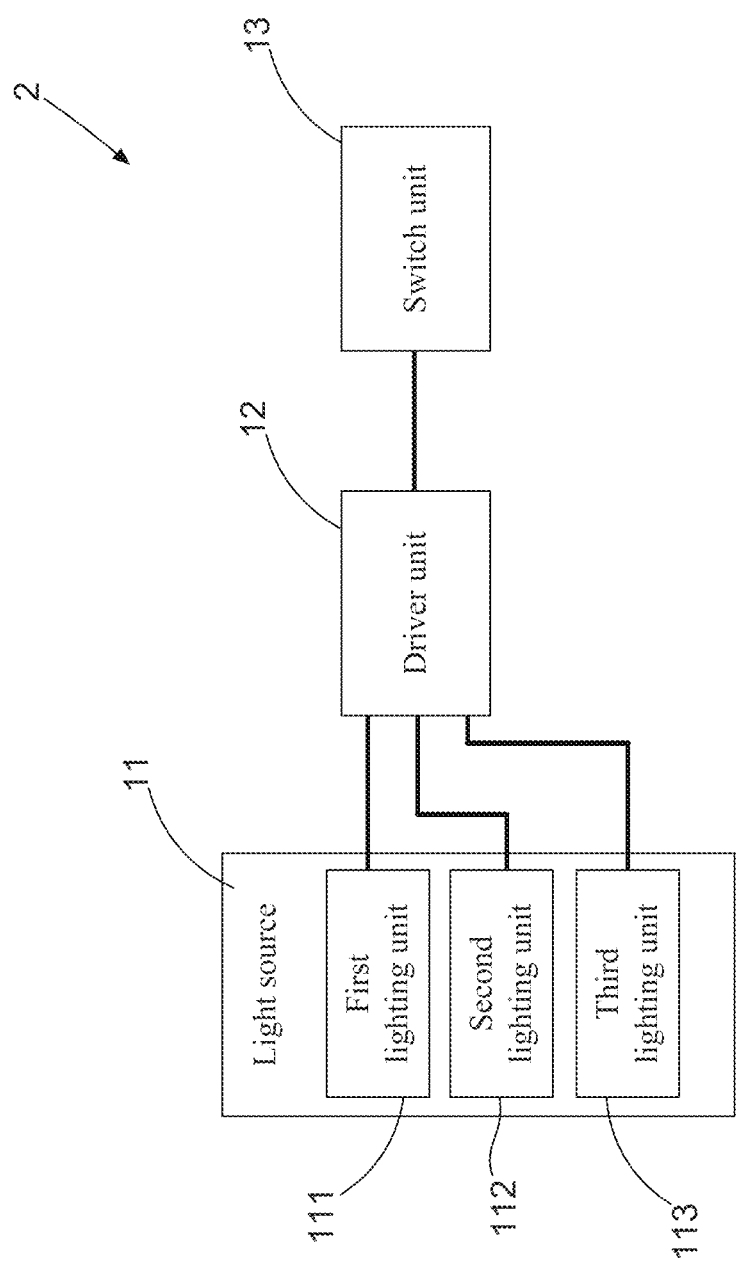
FIG. 8 shows a block diagram of the second embodiment of the illumination device according to the present invention.

With reference to FIG. 7, which shows a stereo diagram of a second embodiment of an illumination device suitable for being applied in light therapy for treating seasonal affective disorder according to the present invention. Moreover, FIG. 8 shows a block diagram of the second embodiment of the illumination device according to the present invention. Particularly, in the second embodiment, the light source 11 of the illumination device 2 further comprises a second lighting unit 112 and a third lighting unit 113. The second lighting unit 112 and the third lighting unit 113 are both electrically connected to the driver unit 12, and are configured for respectively emitting a second light and a third light. According to the particular design of the present invention, the second light has a second wavelength that is in a range between 450 nm and 580 nm, and the third light has a third wavelength that is in a range between 591 nm and 600 nm. In this case, the illumination light provided by the light source 11 is a polychromatic light which consists of the first light, the second light and the third light, and has a maximum color temperature of 1500K.

Figure 9:
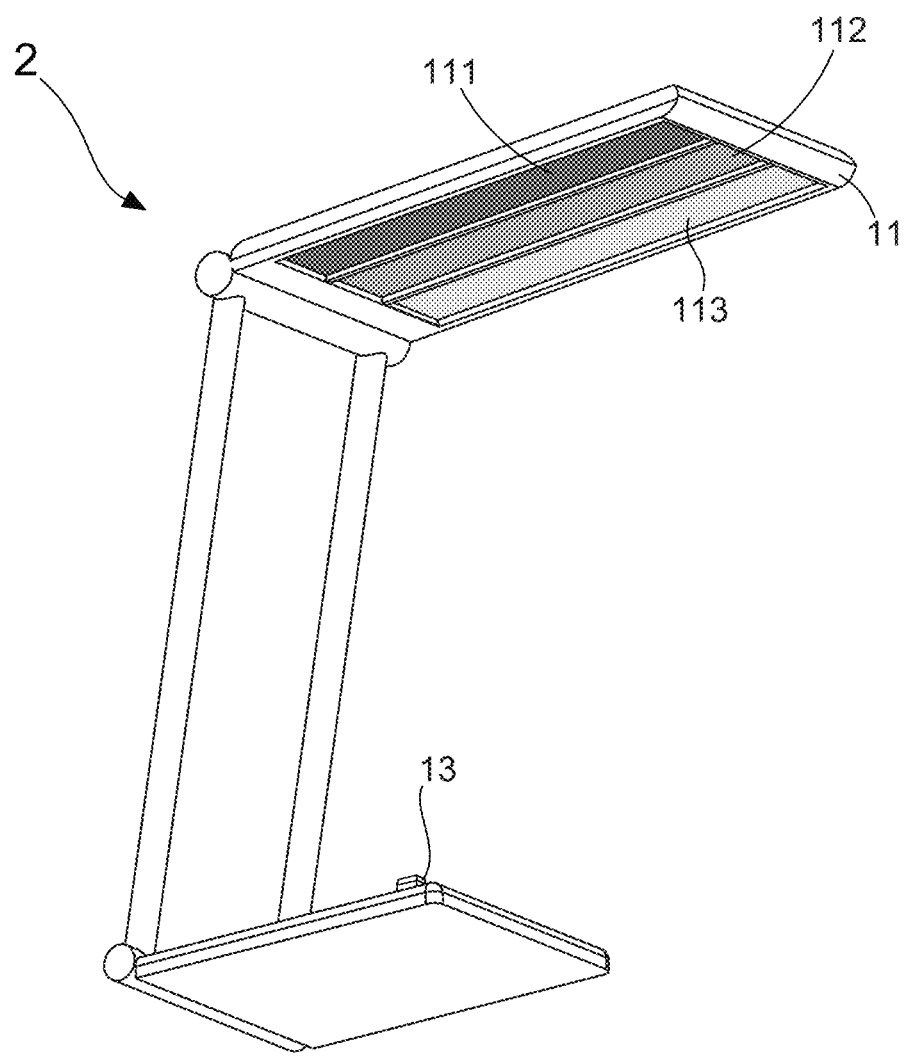
FIG. 9 shows a stereo diagram of a table lamp.
Figure 10:
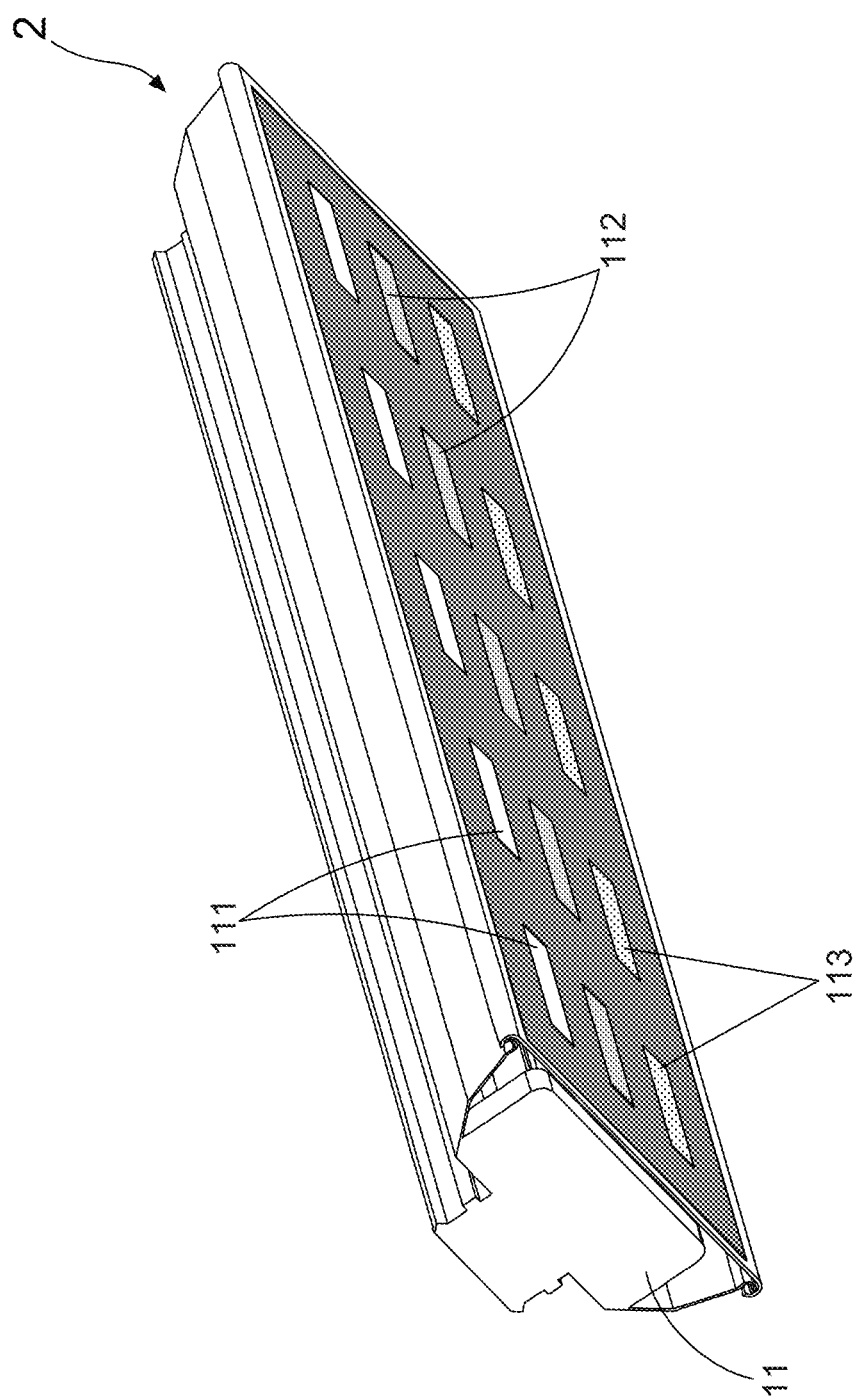
FIG. 10 shows a stereo diagram of a daylight lamp.

FIG. 9 and FIG. 10 show stereo diagrams of a table lamp and a daylight lamp, respectively. In spite of the fact that FIG. 7 depicts that the second embodiment of the illumination device 2 is also presented by a form of light box, it is not meant that the light box is the only one practicable embodiment of the illumination device 2 of the present invention. In a practicable embodiment, the illumination device 2 can also be designed to be a table lamp or a daylight lamp It needs to note that, in the second embodiment, the illumination device 2 with a form of table lamp or daylight lamp is configured to radiate a polychromatic light consisting of the first light, the second light and the third light. Moreover, the polychromatic light has a maximum color temperature of 1500K.

Third Embodiment

Figure 11:
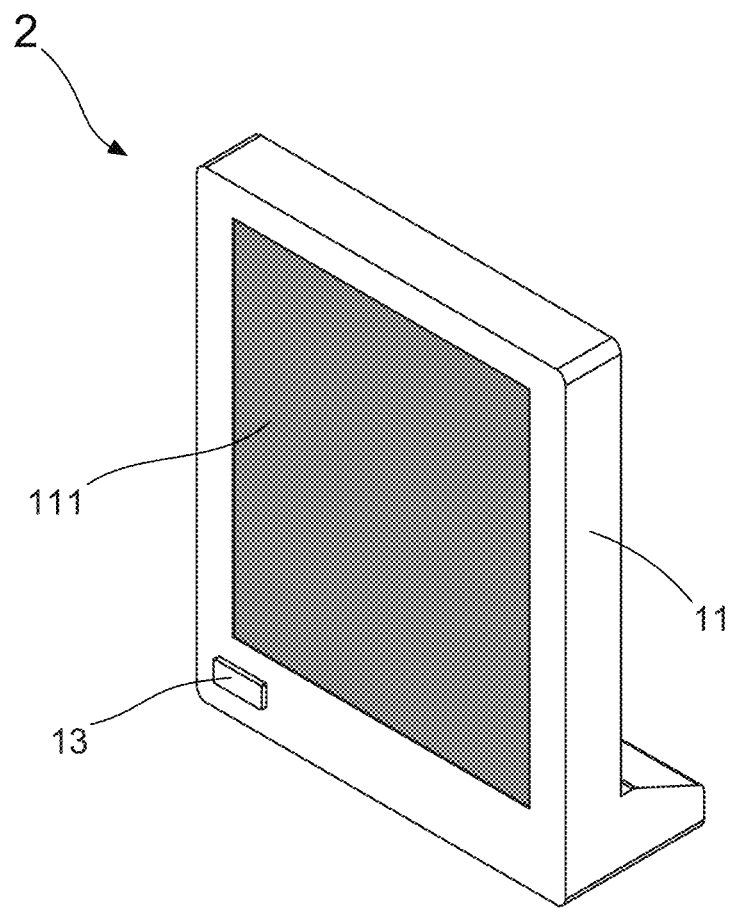
FIG. 11 shows a stereo diagram of a third embodiment of an illumination device suitable for being applied in light therapy for treating seasonal affective disorder according to the present invention.
Figure 12:
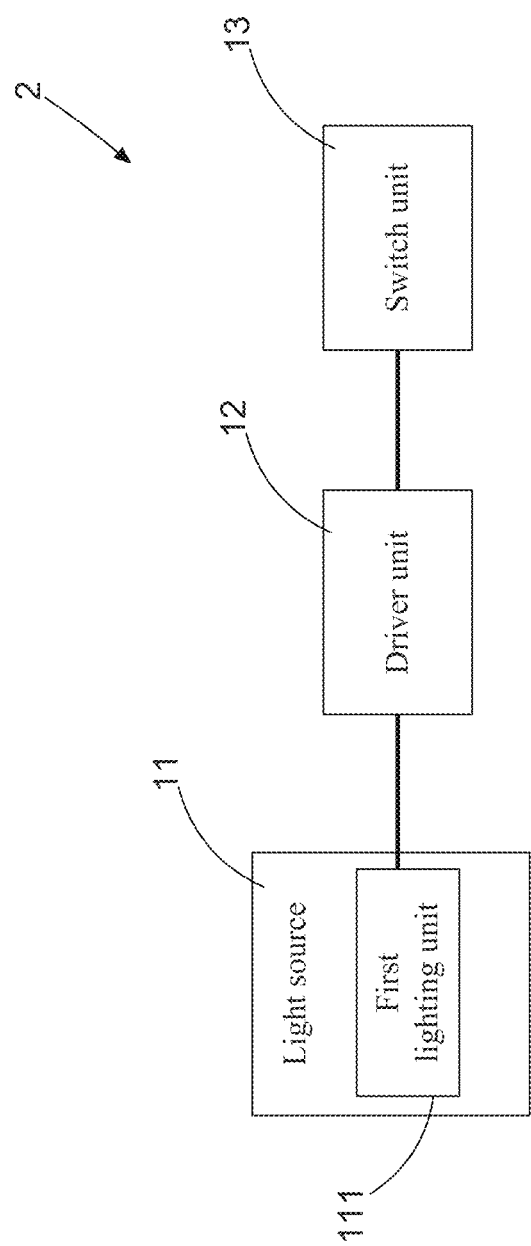
FIG. 12 shows a block diagram of the third embodiment of the illumination device according to the present invention.

With reference to FIG. 11, which shows a stereo diagram of a third embodiment of an illumination device suitable for being applied in light therapy for treating seasonal affective disorder according to the present invention. Moreover, FIG. 12 shows a block diagram of the third embodiment of the illumination device according to the present invention. Differing from above-described first embodiment, the first lighting unit 111 of the light source 11 is particularly configured for emitting a first light, a second light, and/or a third light. In which, the first light has a first wavelength in a range between 581 nm and 590 nm, the second light has a second wavelength in a range between 450 nm and 580 nm and the third light has a third wavelength in a range between 591 nm and 600 nm. In this case, the illumination light provided by the light source 11 of the illumination device 2 consists of the first light, the second light and the third light, and has a maximum color temperature of 1500K.

Figure 13:
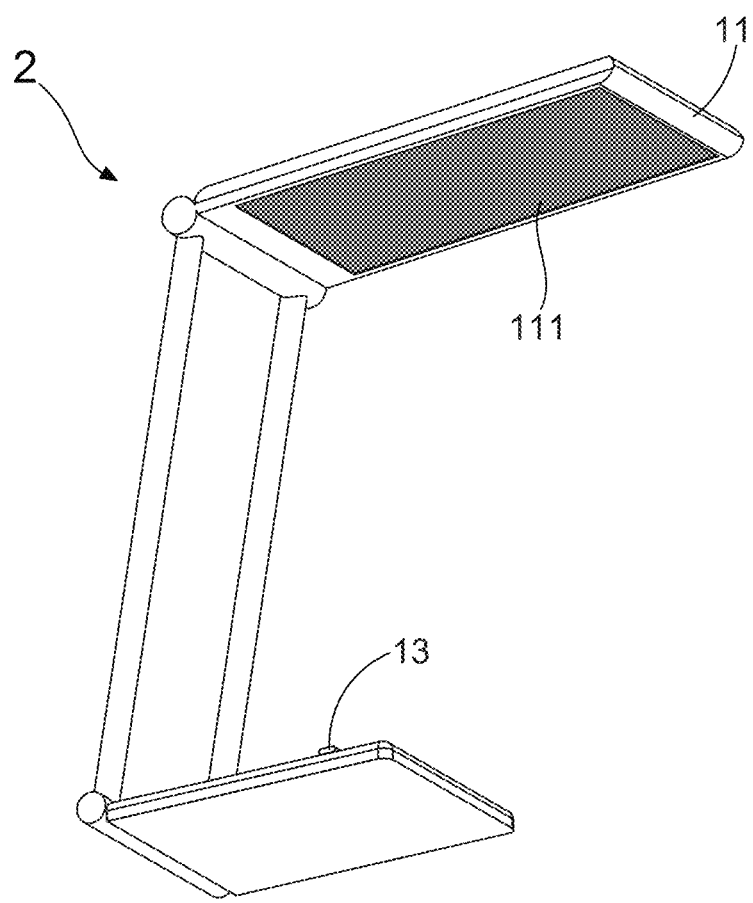
FIG. 13 shows a stereo diagram of a table lamp.
Figure 14:
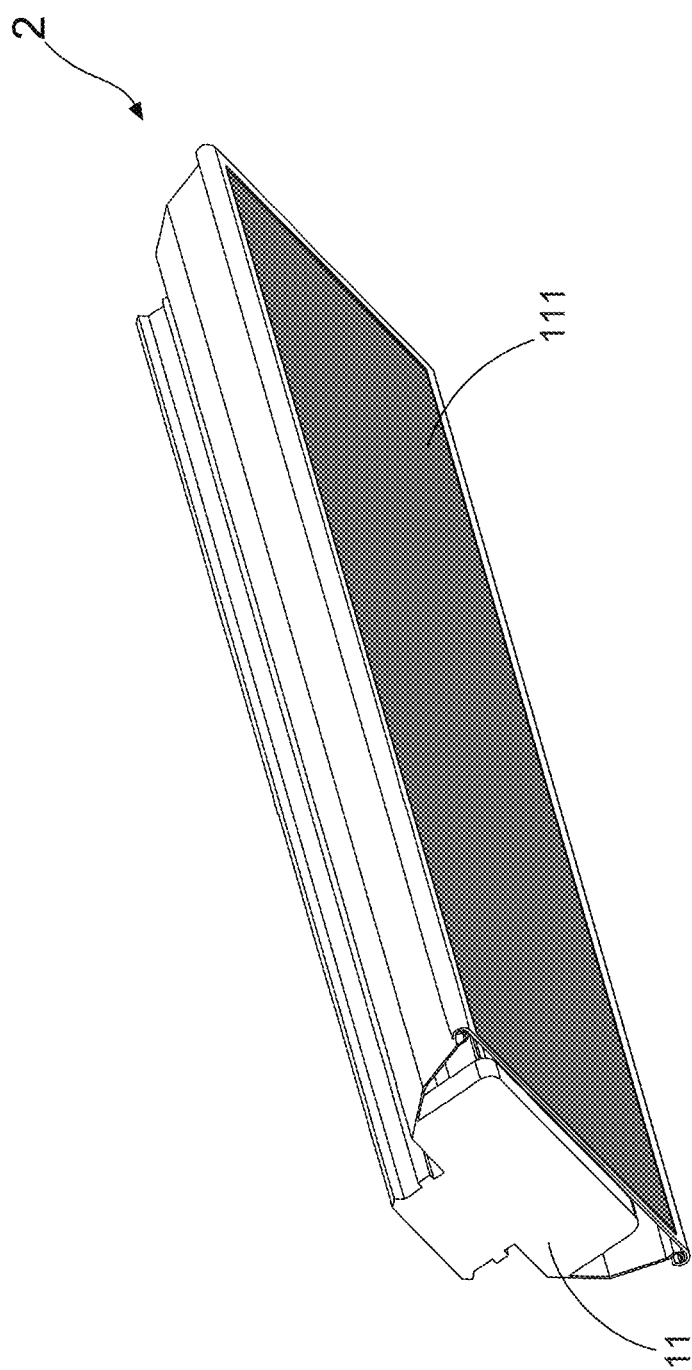
FIG. 14 shows a stereo diagram of a daylight lamp.

FIG. 13 and FIG. 14 show stereo diagrams of a table lamp and a daylight lamp, respectively. In spite of the fact that FIG. 11 depicts that the third embodiment of the illumination device 2 is also presented by a form of light box, it is not meant that the light box is the only one practicable embodiment of the illumination device 2 of the present invention. In a practicable embodiment, the illumination device 2 can also be designed to be a table lamp or a daylight lamp. It needs to note that, in the third embodiment, the illumination device 2 with a form of table lamp or daylight lamp is configured to radiate a polychromatic light consisting of the first light, the second light and the third light. Moreover, the polychromatic light has a maximum color temperature of 1500K.

Fourth Embodiment

Figure 15:
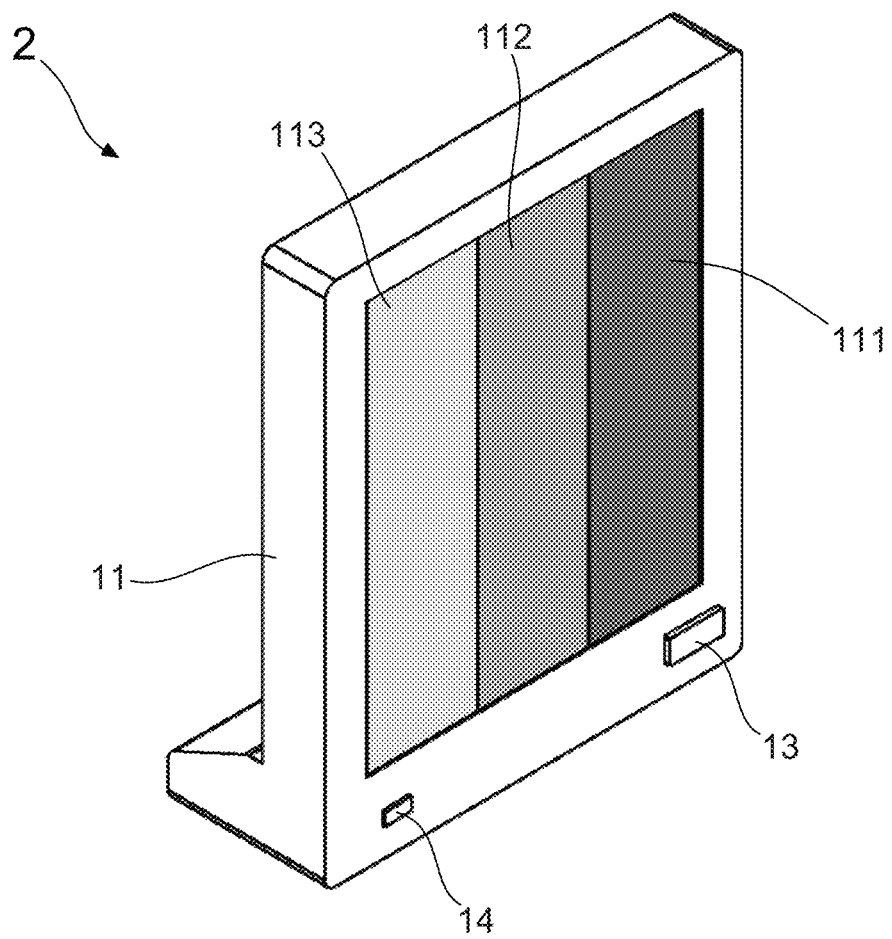
FIG. 15 shows a stereo diagram of a fourth embodiment of an illumination device suitable for being applied in light therapy for treating seasonal affective disorder according to the present invention.
Figure 16:
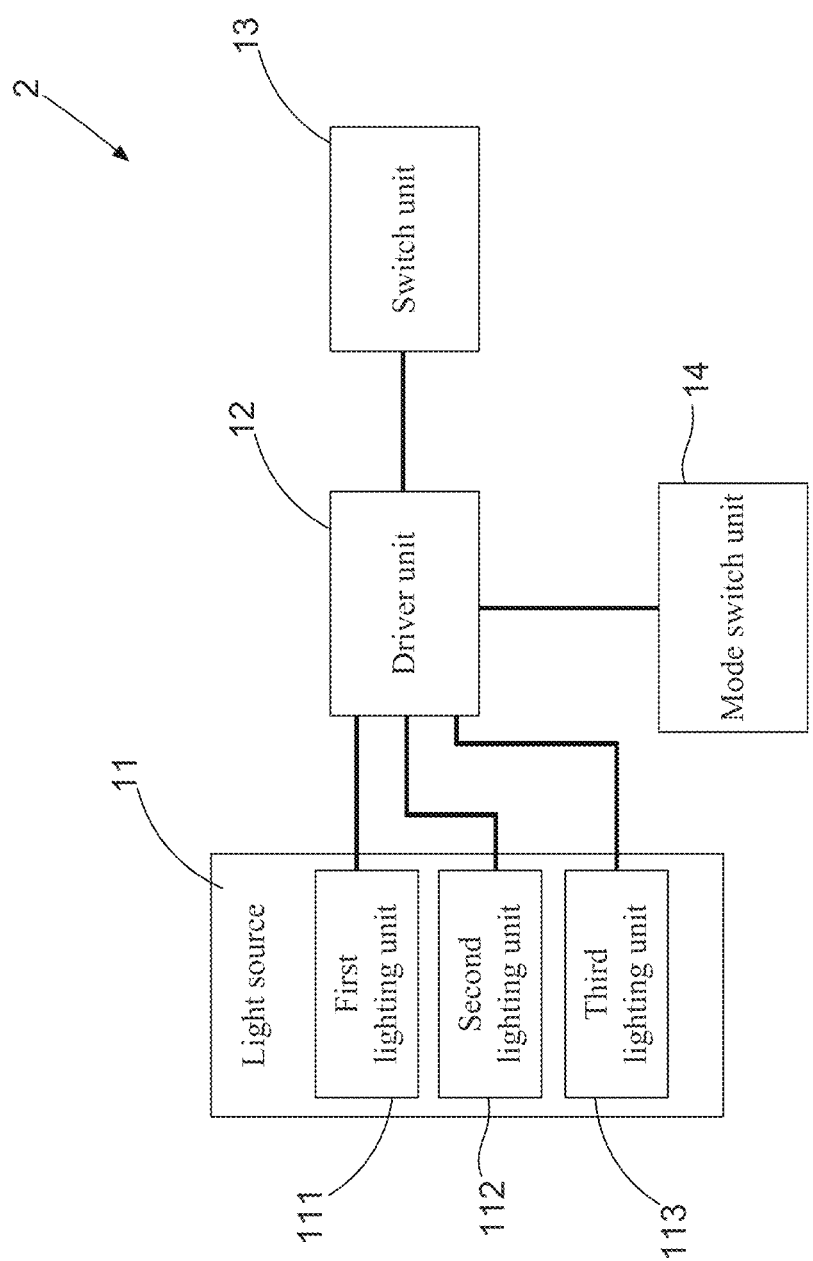
FIG. 16 shows a block diagram of the fourth embodiment of the illumination device according to the present invention.

With reference to FIG. 15, which shows a stereo diagram of a fourth embodiment of an illumination device suitable for being applied in light therapy for treating seasonal affective disorder according to the present invention. Moreover, FIG. 16 shows a block diagram of the fourth embodiment of the illumination device according to the present invention. In the fourth embodiment, the illumination device 2 comprises: a light source 11 comprising a first lighting unit 111, a second lighting unit 112 and a third lighting unit 113, a driver unit 12 electrically connected to the light source 11, a switch unit 13 electrically connected to the driver unit 12, and a mode switching unit 14 electrically connected to the driver unit 12. In the fourth embodiment of the illumination device 2, the mode switching unit 14 is configured for switching the light source 11 to operate in a normal illumination mode or a SAD treatment mode.

As explained in detail below, when the light source 11 is operated in the SAD treatment mode, the illumination light functions as an melatonin secretion inhibitor by guiding the illumination light to irradiate a seasonal affective disorder (SAD) patient. On the other hand, the illumination light provided by the light source 11 consists of the first light, the second light and the third light in the case of the light source 11 being operated in the normal illumination mode, and the illumination light having a maximum color temperature of 1500K.

Figure 17:
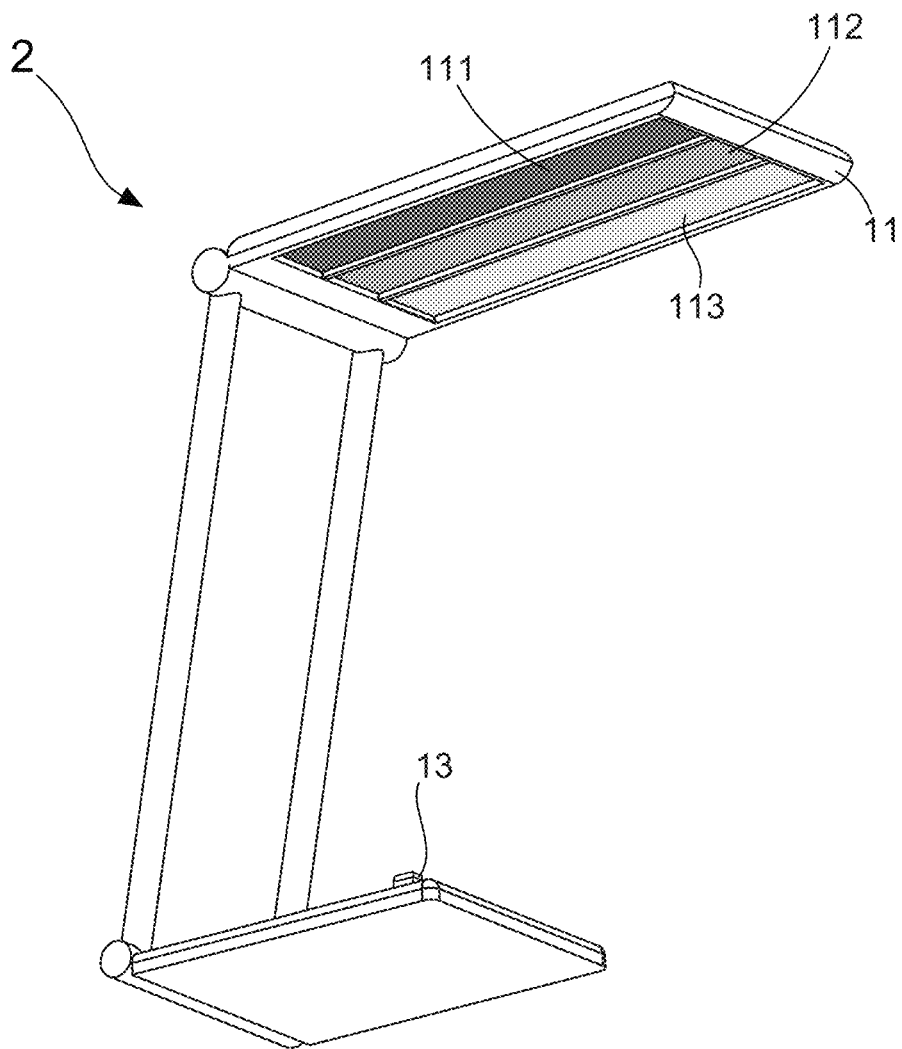
FIG. 17 shows a stereo diagram of a table lamp.
Figure 18:
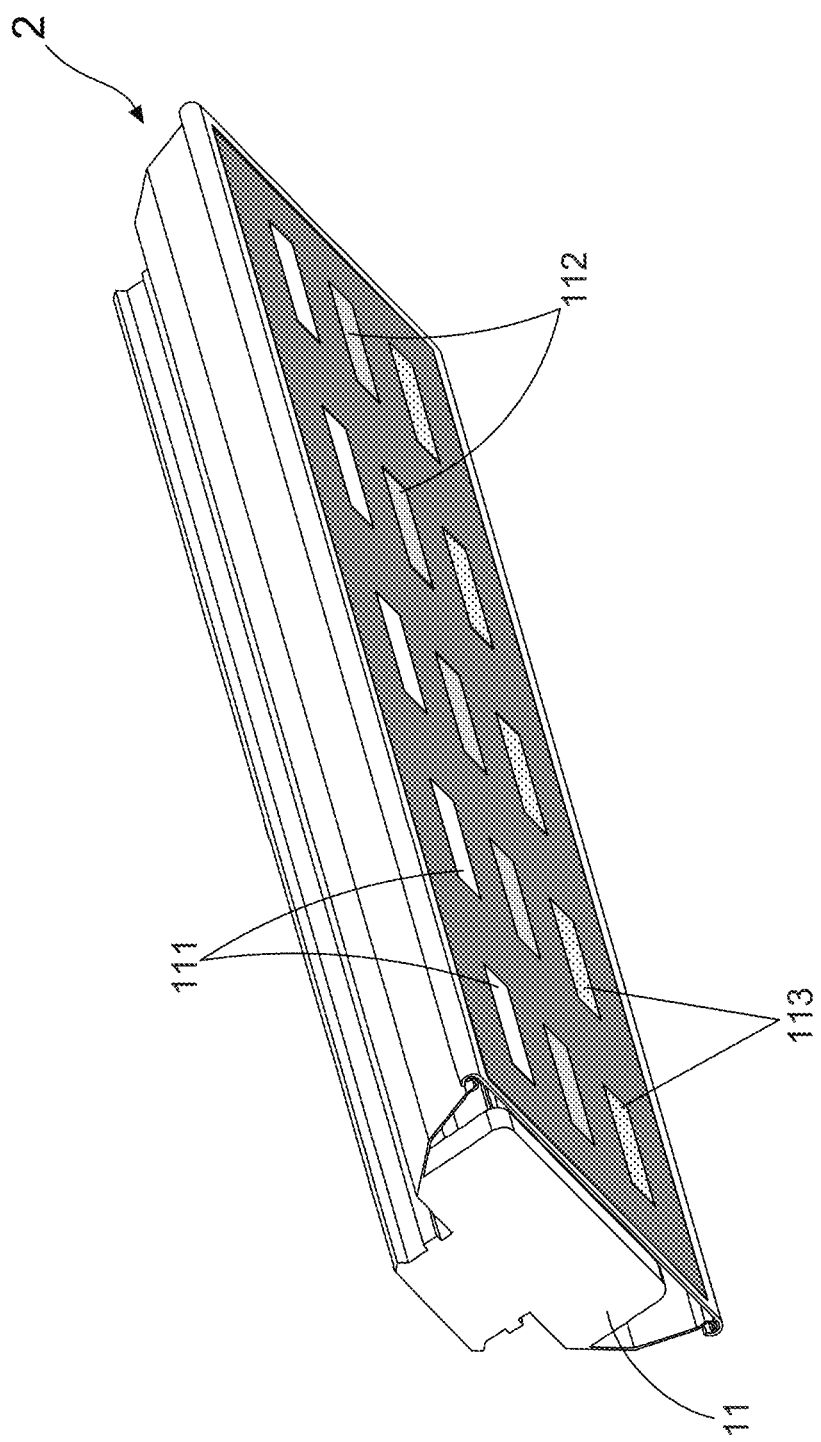
FIG. 18 shows a stereo diagram of a daylight lamp.

FIG. 17 and FIG. 18 show stereo diagrams of a table lamp and a daylight lamp, respectively. In spite of the fact that FIG. 15 depicts that the fourth embodiment of the illumination device 2 is also presented by a form of light box, it is not meant that the light box is the only one practicable embodiment of the illumination device 2 of the present invention. In a practicable embodiment, the illumination device 2 can also be designed to be a table lamp or a daylight lamp. It needs to note that, in the fourth embodiment, the illumination device 2 with a form of table lamp or daylight lamp is configured to further have a mode switching function. When the illumination device 2 works in the SAD treatment mode, the illumination light provided by the light source 11 is a monochromatic light merely consisting of the first light. On the other hand, when the illumination device 2 works in the normal illumination mode, the illumination light provided by the light source 11 is a polychromatic light which consists of the first light, the second light and the third light, and has a maximum color temperature of 1500K.

Figure 6:
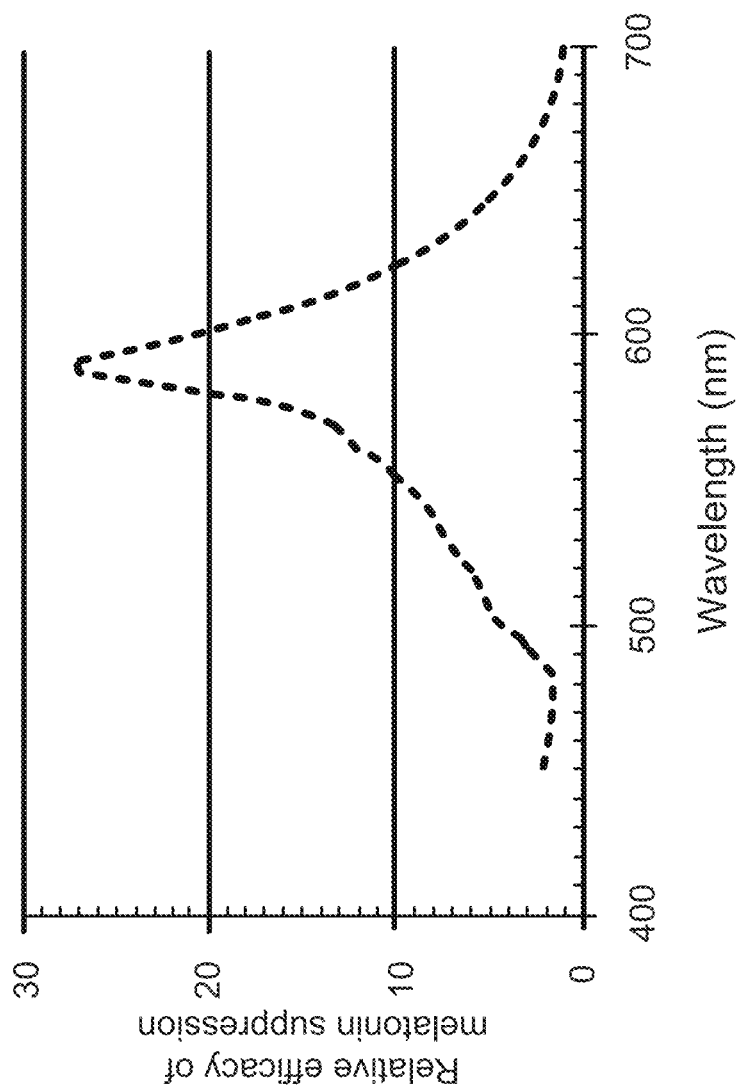
FIG. 6 shows a curve graph of wavelength versus relative efficacy of melatonin suppression.

Herein, it needs to further explain that, each of the first lighting unit 111, the second lighting unit 112 and the third lighting unit 113 comprises at least one lighting element that is selected from the group consisting of organic light-emitting diode (OLED), light-emitting diode (LED) and quantum-dot light-emitting diode (QD-LED). In addition, after completing several experiments, inventors of the present invention have found that visible light exhibits different therapy effects on winter depression with the wavelength ranging from 450 nm to 700 nm. FIG. 6 shows a curve graph of wavelength versus relative efficacy of melatonin suppression. Because the illumination light provided by the light source 11 of the illumination device 2 has a wavelength that is in a range from 581 nm to 590 nm, it is understandable that that such illumination light is classified between a deep-yellow light (588 nm) and a light-orange light (592 nm). Moreover, from data of FIG. 6, it can find that the deep-yellow light or the light-orange light is most effective in suppressing 50% melatonin (MLT) in 3 or 1.5 hours without causing photo-retinitis. That is, FIG. 6 becomes the evidence to prove that the illumination device 2 of the present invention is suitable for use in light therapy, so as to treat seasonal affective disorder (SAD) by way of inhibiting melatonin secretion. Briefly speaking, after a SAD patient receives the irradiation of the illumination light having wavelength ranged in 581-590 nm for a treatment course, the SAD patient is eventually leaded to stay in good spirits and a stable condition of emotion, thereby curing the abnormal symptoms of sleepiness and emotional disorder. Herein, it is worth explaining that, the calculation way of the data shown in FIG. 6 is disclosed in U.S. Pat. No. 8,812,242B2.

Experiments

Subsequently, following paragraphs will provide a variety of experimental data to prove that the illumination device 2 of the present invention is indeed suitable for use in light therapy. In Experiments, inventors of the present invention adopt several LEDs to emit a plurality of lights, wherein each of the lights has a specific wavelength in a range between 400 nm and 700 nm. Consequently, in the case of referring standard calculating formulas published by Occupational Safety and Health Administration (OSHA), inventors of the present invention calculate and collect data of maximum permissible exposure (MPE) limit of retina and data of retina illuminance of each of the lights. Related experimental data have collected and listed in following Table (1), Table (2) and Table (3).

TABLE (1)

| λ (nm) | Relative efficacy of melatonin suppression | MPE limit of retina (second) (@100 lx) | retina illuminance (lx) (@ MPE= 10000秒) | maximum retina illuminance (lx) (@ MPE = 30 minites) |
|---|---|---|---|---|
| 400 | — | 1 | <0.01 lx | <0.056 lx |
| 450 | 2.1 | 707 | <0.07 lx | <0.389 lx |
| 495 | 3.4 | 313 | <3.13 lx | <17.39 lx |
| 560 | 12.0 | 26902 | <269 lx | <1494 lx |
| 588 | 27.0 | 81140 | <811 lx | <4506 lx |
| 635 | 7.0 | 35618 | <356 lx | <1978 lx |
| 700 | 1.0 | 707 | <7.07 lx | <39.28 lx |

TABLE (2)

| λ (nm) | Maximum retina illuminance (lx) for MPE limit = 6.5 hours | Retina illuminance (lx) for making melatonin suppression rate reach to 50% within 6.5 hours | Maximum retina illuminance (lx) for MPE limit = 6.5 hours | Retina illuminance (lx) for making melatonin suppression rate reach to 50% within 1.5 hours |
|---|---|---|---|---|
| 400 | <0.0093 | — | <0.019 | — |
| 450 | <0.065 | 0.4 | <0.13 | 0.7 |
| 495 | <2.9 | 9.2 | <5.8 | 17.7 |
| 560 | <249 | 228 | <498 | 441 |
| 588 | <751 | 414 | <1502 | 801 |
| 635 | <330 | 440 | <659 | 851 |
| 700 | <6.1 | 53.9 | <13.1 | 104 |

TABLE (3)

| λ (nm) | Maximum retina illuminance (lx) for MPE limit = 6.5 hours | Retina illuminance (lx) for making melatonin suppression rate reach to 45% within 6.5 hours | Maximum retina illuminance (lx) for MPE limit = 1.5 hours | Retina illuminance (lx) for making melatonin suppression rate reach to 35% within 1.5 hours |
| --- | --- | --- | --- | --- |
| 400 | <0.0093 | — | <0.019 | — |
| 450 | <0.065 | 0.3 | <0.13 | 0.3 |
| 495 | <2.9 | 7.4 | <5.8 | 7.4 |
| 560 | <249 | 184 | <498 | 184 |
| 588 | <751 | 334 | <1502 | 334 |
| 635 | <330 | 355 | <659 | 355 |
| 700 | <6.1 | 44 | <13.1 | 44 |

Figure 1:
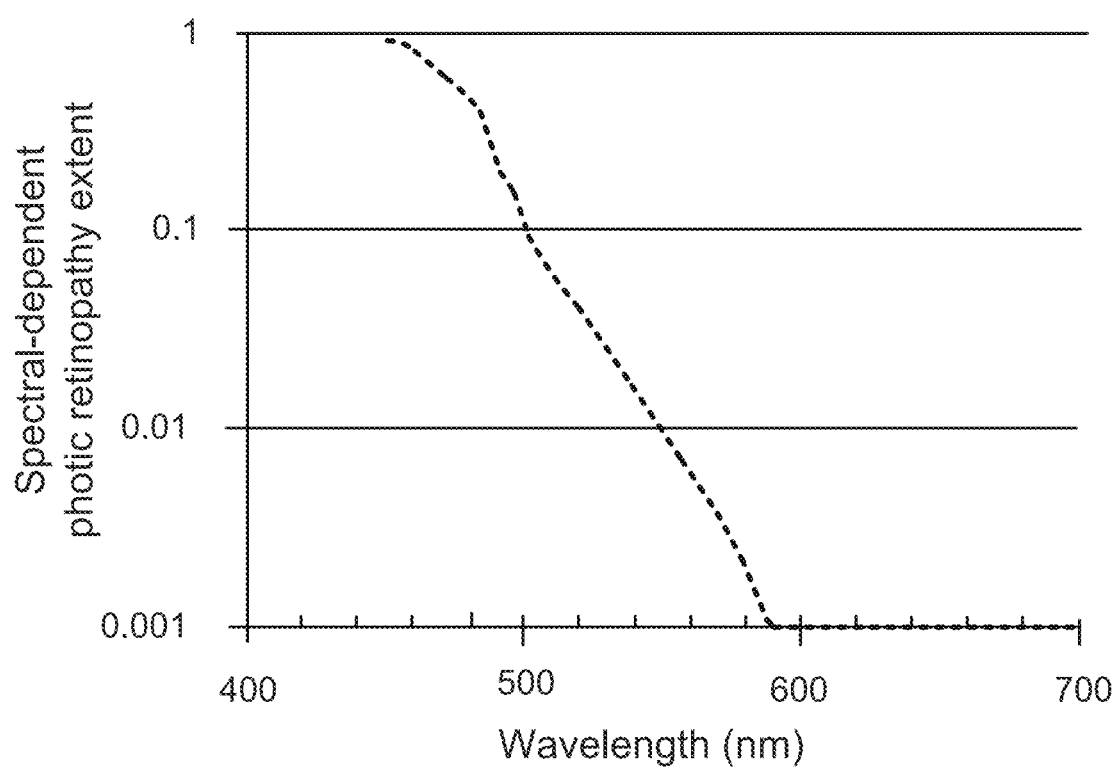
FIG. 1 shows a curve graph of wavelength versus spectral-dependent photic retinopathy extent.

From the Table (1), it is observed that the deep-yellow light (588 nm) exhibits a retina MPE limit of 81140, and that is greater than that of other monochromatic lights in the case of constant illuminance. Moreover, the deep-yellow light (588 nm) also shows the most effective efficacy in inhibiting melatonin secretion than that of other monochromatic lights. Therefore, it is understood that, using deep-yellow light (588 nm) as a melatonin secretion inhibitor for use in inhibiting melatonin secretion is not only able to achieve a treatment effect on curing seasonal affective disorder (SAD) without causing photo-retinitis. In addition, data of FIG. 1 also indicate that the deep-yellow light has a maximum retina illuminance of 4506 1x in the case of a retina MPE limit being 30 minutes. Moreover, On the other hand, data of Table (2) report that, the deep-yellow light (588 nm) has a maximum retina illuminance of 751 1x (or 1502 1x) in the case of a retina MPE limit being 6.5 hours (or 1.5 hours). Moreover, after receiving the irradiation of the deep-yellow light having illuminance of 414 1x (or 801 1x) for 6.5 hours (or 1.5 hours), the relative suppression rate of melatonin is up to 50%. In addition, data of Table (3) further prove that, after receiving the irradiation of the deep-yellow light having illuminance of 334 1x for 6.5 hours, the relative suppression rate of melatonin reaches to 45%. Moreover, after receiving the irradiation of the deep-yellow light having illuminance of 334 1x for 1.5 hours, the relative suppression rate of melatonin reaches to 35%.

As a result, experimental data of FIG. 6, Table (1), Table (2), and Table (3) have proved that, the illumination device 2, configured for emitting an illumination light with a specific wavelength that is in a range between 581 nm and 590 nm, is able to functions as a melatonin secretion inhibitor for use in light therapy, so as to treat seasonal affective disorder (SAD) by way of inhibiting melatonin secretion. Moreover, experimental data have also proved that, after a SAD patient receives the irradiation of the illumination light having wavelength ranged in 581-590 nm for a treatment course, the SAD patient is eventually leaded to stay in good spirits and a stable condition of emotion, thereby curing the abnormal symptoms of sleepiness and emotional disorder without causing photo-retinitis.

The above description is made on embodiments of the present invention. However, the embodiments are not intended to limit scope of the present invention, and all equivalent implementations or alterations within the spirit of the present invention still fall within the scope of the present invention.

What is claimed is:

1. An illumination device, being configured for use in light therapy for treating seasonal affective disorder (SAD), and comprising:
  a light source, comprising at least one first lighting component, at least one second lighting component, and at least one third lighting component;
  a driver circuit, being electrically connected to the light source, so as to drive the first lighting component, the second lighting component and the third lighting component to emit a first light, a second light and a third light, respectively; wherein the first light has a first wavelength in a range between 581 nm and 590 nm, the second light having a second wavelength in a range between 450 nm and 580 nm, and the third light has a third wavelength in a range between 590 nm and 620 nm;
  a power switching unit, being electrically connected to the driver circuit, and being configured to switch the driver circuit on or off; and
  a mode switching unit, being electrically connected to the driver circuit, and being configured to switch the driver circuit to work in a normal illumination mode or a light therapy mode;
  wherein in case the driver circuit works in the light therapy mode, the driver circuit drive the light source to radiate a first illumination merely containing the first light;
  wherein in case the driver circuit works in the normal illumination mode, the driver circuit drive the light source to radiate a second illumination containing the first light, the second light and the third light, and the second illumination having a color temperature that is equal to or smaller than 1500K.

2. The illumination device of claim 1, wherein the first lighting component, the second lighting component and the third lighting component are all selected from a group consisting of organic light-emitting diode (OLED), light-emitting diode (LED) and quantum-dot light-emitting diode (QD-LED).

* * * * *